United States Patent [19]

Gendrich et al.

[11] Patent Number: 4,491,660
[45] Date of Patent: Jan. 1, 1985

[54] MATRIX POLYMERS FOR BINDING ENDOTOXINS

[75] Inventors: Ronald L. Gendrich, Waukegan; William H. Holleman, Libertyville, both of Ill.

[73] Assignee: Abbott Laboratories, North Chicago, Ill.

[21] Appl. No.: 374,442

[22] Filed: May 3, 1982

Related U.S. Application Data

[63] Continuation-in-part of Ser. No. 110,871, Jan. 10, 1980, abandoned.

[51] Int. Cl.$^3$ .............................................. C07H 1/00
[52] U.S. Cl. ........................................ 536/32; 525/296; 525/303; 525/418; 536/1.1; 536/18.7; 536/22; 536/30; 536/43; 536/55.1; 536/55.3; 536/58; 536/63; 536/84; 536/115; 536/119; 536/120; 536/124; 424/180
[58] Field of Search ..................... 536/1.1, 18.7, 55.3, 536/55.1, 22, 63, 53, 84, 30, 32, 120; 525/296, 303, 336, 418; 424/180

[56] References Cited

U.S. PATENT DOCUMENTS

| | | | |
|---|---|---|---|
| 4,020,268 | 4/1977 | Hirotoshi et al. | 536/1.1 |
| 4,022,962 | 5/1977 | Diamond | 536/18.7 |
| 4,025,622 | 5/1977 | Ogura et al. | 536/18.7 |
| 4,185,090 | 1/1980 | McIntire | 536/1.1 |

OTHER PUBLICATIONS

Giul Badamova, et al., "Probl. Germalol Perelir Krovi", vol. 11, No. 7, pp. 19–23, 1966.
Saunders, et al., "Ion Exchange Process Ind.," Pap. Conf., 70, pp. 410–415, 1970.
Romanowska, "Analytical Biochemistry", vol. 33, pp. 383–389, 1970.
Rubio, "Jour. Chromatogr.", 57, pp. 148–150, 1971.
Bader, et al., "Z. Naturforsch", vol. 28, No. 7, pp. 422–430, 1973.
Nolan, et al., "Proceedings of the Society for Experimental Biology and Medicine", 149, pp. 766–770, 1975.
Romanowska, et al., 37 Febs Letters", vol. 66, No. 1, pp. 82–85, 1976.

*Primary Examiner*—Johnnie R. Brown
*Attorney, Agent, or Firm*—James L. Wilcox

[57] ABSTRACT

An endotoxin binding material affixed to a support is disclosed. One embodiment is a matrix material capable of binding endotoxins and comprising a polar, water-insoluble, high molecular weight polymer support to which is attached groups which adsorb endotoxin molecules. The groups comprise bifunctional aliphatic molecules, one end of which is bound to the support, the other end of which is bound to an aryl molecule. The invention has utility in the removal of endotoxins from biological fluids and other solutions and for concentrating endotoxins so that they may be subsequently detected and quantified.

5 Claims, No Drawings

MATRIX POLYMERS FOR BINDING ENDOTOXINS

REFERENCE TO RELATED APPLICATION

This application is a continuation-in-part of application Ser. No. 110,871, filed Jan. 10, 1980, now abandoned.

BACKGROUND OF THE INVENTION

Various bacterial products have the capability to exert undesirable effects on humans and other animals. Endotoxins are toxic materials released by bacterium on bacterial lysis and are distinguished from the toxic substances synthesized and excreted by the intact bacterium, namely exotoxins. While endotoxins were first recognized for their ability to induce fever, they are now known to have a broad spectrum of biologic activities. On bacteriolysis, endotoxins consisting of aggregates of lipopolysaccharides and protein and to some extent loosely bound lipids, are released from the bacterium into the surrounding medium. Thus, endotoxins consist primarily of lipopolysaccharides (LPS) with various amounts of protein and lipid. Since it has been demonstrated that almost all of the biologic activities usually attributable to bacterial endotoxins can also be elicited with isolated chemically pure lipopolysaccharides, the terms "endotoxins" and "lipopolysaccharides" have been utilized interchangeably to some extent.

Pyrogens, particularly endotoxins or lipopolysaccharides, are constituents of the cell wall of Gram-negative bacteria. When admitted to the circulation of animals, these materials trigger a chain of biochemical reactions which lead to the production of an elevated body temperature or fever; hence, the name pyrogens. Removal of pyrogens from pharmaceutical preparations intended for parenteral use has long been a problem due to the ubiquitous distribution, detergent-like properties and the stability of the endotoxin molecules and the extreme potency of their fever-inducing activity. Current conventional methods for the removal of pyrogens employ either roasting, strong acid or base treatment, or chemical oxidation, none of which is an acceptable treatment for use with sensitive pharmaceutical preparations. Ultrafiltration is an effective method for sensitive preparations, but is useful only for low (less than 10,000 MW) molecular weight preparations. Molecular sieve chromatography has the same limitations as ultra filtration. Thus, there is no current method of general applicability for removal of pyrogens from macromolecular preparations.

In the administration of intravenous fluid, it is imperative that no endotoxins be administered to the patient. Although intravenous fluids are processed so as to eliminate any microorganisms, such as by autoclaving, for example, in intravenous therapy it is common to use a filter at the time of administration in an attempt to remove any microorganism which may remain in the fluid. Such filters are described, for example, in U.S. Pat. Nos. 3,854,907 and 4,101,423. These filters are not effective to remove endotoxins.

A current means of detecting and quantitating endotoxin in vitro is the Limulus Amoebocyte Lysate method (LAL) as described in the New England Journal of Medicine, Vol. 289, No. 18, pages 931 to 934, Nov. 1, 1973. Limulus amoebocyte lysate is an aqueous extract of blood cells (amoebocytes) from the horseshoe crab, *Limulus polyphemus*. LAL forms a firm clot when incubated with endotoxins and can be used to detect small quantities of endotoxin. A limulus lysate of improved sensitivity is described in U.S. Pat. No. 4,107,077, granted Aug. 15, 1978. LAL is sold commercially under the trademark Pyrotell by Associates of Cape Cod, Inc. and is used in the detection and quantitation of endotoxin.

SUMMARY OF THE INVENTION

The invention comprises an endotoxin binding material affixed to a support. One embodiment is a matrix material capable of binding endotoxins and which comprises a water insoluble, high molecular weight polymer support to which is bound selected groups. The groups comprise bifunctional alkyl moieties bound to the support and an aromatic moiety to which in turn may be bound a neutral or positively charged group. The matrix material is capable of binding endotoxins and can be utilized in the removal of endotoxins from biological fluids or other solutions, or for concentrating and insolubilizing endotoxins so that they may be subsequently detected and quantified. For diagnostic purposes in particular, the endotoxin binding material can be affixed to a test tube wall, plastic beads, particles and the like.

The invention can be used to remove endotoxins or pyrogens from concentrates of pharmaceutical preparations to be administered parenterally, as a step in manufacture; to concentrate LPS from urine samples of patients suspected of having Gram-negative infections; to concentrate LPS from samples of water supplies as a means of testing the burden of enteric contamination; to remove Gram-negative bacteria from supplies of fuel oil to be stored for substantial periods of time; to concentrate endotoxin from the serum of patients suspected of being in a state of endotoxemia; to concentrate LPS from samples of cerebrospinal fluid of patients suspected of being in a state of endotoxemia; to remove pyrogens from parenteral solutions prior to administration to a patient; and to concentrate endotoxins in a form suitable for subsequent quantification. The material may be utilized in the form of a column or cartridge, for example.

DETAILED DESCRIPTION OF THE INVENTION

The invention comprises an endotoxin binding material affixed to a support. One embodiment is a matrix material capable of binding endotoxins, said matrix material having the formula:

A-x-B-y-Z wherein A is an insoluble polymer; x is a first linking group comprising isourea, an ester, an ether, or an amine; B is a spacer group comprising a straight, branched or cyclic alkyl of from 1–12 carbon atoms, hydroxyl loweralkylamine, loweralkylether, or loweralkylthioether; y is a second linking group comprising a methylene, an ether, thioether or an amide; and Z is an aryl nucleus group, either unsubstituted or substituted with one or more amidino, guanidino, amino, carboxamido, hydroxyl, halo, nitro, alkyl or alkoxy.

An example of a suitable matrix material is agarose-isoureido-hexanoyl-meta-benzamidineamide,

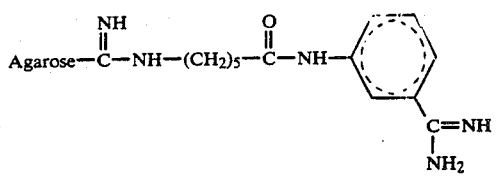

Suitable support substances include cellulose, cellulose acetate or nitrate, agarose, polymethacrylate or polystyrene.

Some examples of matrix materials differing in composition of the spacer (B) are as follows:

Support-Link 1-Spacer-Link 2-Aryl Nucleus

—C$_4$H$_8$—
—C$_5$H$_{10}$—
—C$_6$H$_{12}$—
—C$_7$H$_{14}$—
—C$_{11}$H$_{22}$—

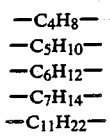

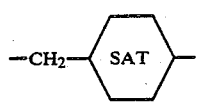

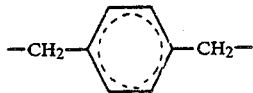

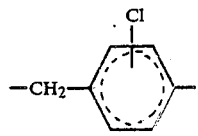

—(CH$_2$)$_2$—NH—(CH$_2$)$_2$—
—(CH$_2$)$_3$—S—(CH$_2$)$_3$—

Examples of matrix materials differing in composition of the second linking group are as follows:

Support-Link 1-Spacer-Link 2-Aryl Nucleus

—CH$_2$—

—S—
—O—

The following are examples of matrix materials differing in composition of the aryl molecule:

Support-Link 1-Spacer-Link 2-Aryl Molecule

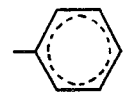 phenyl

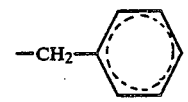 benzyl

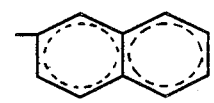 naphthyl

Examples of matrix materials differing in composition of the substituted Aryl group:

Support-Link 1-Spacer-Link 2-Substituted Aryl Group

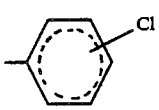 chloro

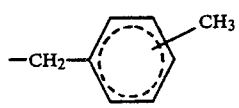 methyl

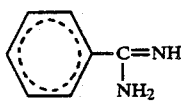 amidine

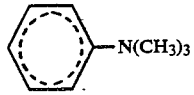 trimethylamino

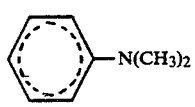 dimethylamino

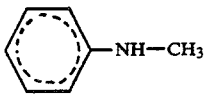 methylamino

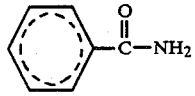 amide

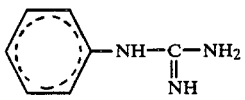 guanidinium

 dichloro

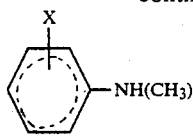

X = Halogen or loweralkoxy

The term "loweralkyl", as used herein, refers to straight or branched chain alkyl radicals containing from 1 to 6 carbon atoms including but not limited to methyl, ethyl, n-propyl, iso-propyl, n-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "alkyl" refers to straight, branched or cyclic alkyl radicals containing from 1 to 12 carbon atoms.

The term "aryl" includes phenyl, naphthyl or benzyl.

The term "substituted aryl" includes aryl groups substituted by secondary, tertiary or quaternary ammonium, amidinium or guanidinium or by one or more halo or loweralkoxy.

EXAMPLE 1

PREPARATION AND TESTING OF AGAROSE BASED MATRIX MATERIAL

Agarose-6-aminohexanoic acid isourea 45 gm of 6-aminohexanoic acid, suspended in 25 ml water, is mixed with 100 ml of packed Sepharose ™ (agarose gel beads). The pH of the mixture is adjusted to 10.5 by the addition of a saturated solution of NaOH in water. The temperature of the suspension is adjusted to 15° C. by the addition of chunks of ice. Eighty grams of solid CNBr is added to the suspension over a 15 minute period. Rapid stirring is maintained. The pH is maintained at 10.5±0.5 by the addition of saturated NaOH. The temperature is maintained at 17.5°±2.5° C. by the addition of ice. After the reaction mixture has stopped consuming base, excess reagents are removed by filtering the solid, derivatized agarose on a coarse sintered glass filter, then washing it in place by the addition of several bed volumes of 1 M NaCl, then several bed volumes of 1 N acetic acid, finally with at least 5 bed volumes of water.

Agarose-6-aminohexanoyl (isourea)-meta benzamidine amide

The suspension of Agarose-6-aminohexanoic acid isourea is then transferred to a beaker, adding about 250 ml water. Fifty grams of 1-ethyl-3-(3 dimethylaminopropyl) carbodiimide (EDC) are added as solids. The EDC dissolves rapidly and reacts with the agarose derivative to form an active ester. The suspension is stirred 30 minutes to permit the active ester formation to occur. Ten grams of meta-amino benzamidine hydrochloride in water solution, neutralized to pH 4, is then added. The pH of the reaction is adjusted to 4.5±0.5 and maintained at that value for 24 hours, preferably at 4° C. A sample is then removed.

The degree of substitution of the sample is determined by the indirect method of Hoare and Koshland, JBC 242, 244 (1967).

The degree of substitution was 12.75±0.25 ueq. 6-aminohexanoic acid (6AHA)/ml of beads. The degree of incorporation of benzamidine was 11.6 ueq/ml gel or 91% of the 6AHA.

Covering unreacted carboxyl groups to eliminate cation exchange property

An additional 50 grams of EDC are then added to the suspension. 6 molar ethanolamine HCl, pH 6±1, is then added to a final ethanolamine concentration of 0.4 M. The pH is maintained at 5.0±0.5 for an additional 24 hours. The product, SAB, is now washed as above wit 3 bed volumes of 1 M NaCl solution, with 3 bed volumes of N acetic acid and with 3 bed volumes of water. If extended storage is required, the addition of 0.1% trichlorobutanol in the final wash is useful as a preservative.

Testing of Matrix Material for Binding of Endotoxin 1 cc colums are packed with Sepharose ™, Agarose-6-aminohexanoic acid isourea, or with the finished SAB. To each column is added a solution containing 13.6 ugm of endotoxin derived from E. coli and labeled with $^{51}$Cr. The endotoxin-containing solution is washed through the columns with 20 column volumes of water. The wash solutions are counted to estimate the amount of endotoxin which has not been adsorbed by the columns.

| Adsorbant Tested | % Breakthrough | % Adsorbed |
|---|---|---|
| Sepharose-4B ™ | 86.9 | 13.1 |
| Agarose-6-aminohexanoic acid isourea | 89.2 | 10.8 |
| SAB | 0.4 | 99.6 |

Thus, the completed SAB is demonstrated to be highly efficacious in the removal of endotoxin from solution.

EXAMPLE 2

PREPARATION AND TESTING OF CELLULOSE BASED MATRIX MATERIAL

Crude cotton fiber, microgranular cellulose (Whatman CC31) and microcrystalline cellulose (Avicel) were each derivatized via the method of Example 1. Columns of each derivative were prepared, each column containing 100 ul bed volume of packed support. A challenge of 40 ugm $^{51}$Cr-labeled LPS from E. coli was applied to each column and the columns washed with 20 column volumes of 0.15M NaCl in water. The wash solution was counted for $^{51}$Cr. The loss of $^{51}$Cr from solution indicates the efficiency of endotoxin removal.

| Polymer | % LPS Adsorbed ($^{51}$Cr Loss from Solution) |
|---|---|
| Microcrystalline Cellulose | 99.2 |
| Microgranular Cellulose | 98.6 |
| Crude cotton fibers | 47.2 |

This data demonstrates the utility of various forms of cellulose as the polymeric support of this invention.

EXAMPLE 3

PREPARATION AND TESTING OF CELLULOSE DERIVATIVE

A Cellulose nitrate/Cellulose acetate composite (Millipore 0.22 u retention filtration membrane) was reacted by the method of Example 1. The degree of substitution was determined to be 2.3 umol/gram composite.

The starting material and the Product were both tested for their ability to bind endotoxin. Samples of starting material and product were contacted with 2 ugm of endotoxin labelled with $^{51}Cr$ for quantification. After 15 minutes of contact, the materials were washed exhaustively with 0.15M NaCl solution. The samples were then counted to determine the amount of $^{51}Cr$ labelled endotoxin which had bound to the materials.

| Material Tested | % of Endotoxin Bound |
|---|---|
| Cellulose Nitrate/ Acetate composite | 15.6 ± 12 (Standard derivation) |
| Product | 121 ± 6.4 |

Thus, we have shown that Cellulose nitrate/cellulose acetate composite, commonly used in the preparation of sterilizing filters, can be derivatized to yield a material useful in the adsorbtion of endotoxin.

EXAMPLE 4

REMOVAL OF LPS FROM VARIOUS FLUIDS

Columns were prepared using 100 ul packed volume of the matrix material prepared in Example 1. 50 ugm of $^{51}Cr$-labeled LPS, dissolved in various solutions, were percolated through each column, then the column washed with 10 bed volumes water. The loss of $^{51}Cr$ label from solution indicates the efficacy of the removal of LPS.

| Solution Composition | LPS % Adsorbed |
|---|---|
| 0.1 N HCl | 85 |
| 0.1 N acetic acid | 100 |
| 0.01 M phosphate buffer, pH 7.5 | 97.2 |
| 3% NaCl | 96.9 |
| Phosphate buffered saline, pH 7.4 | 100 |
| 0.1 M NaOH | 97.2 |

Thus, the invention is capable of sequestering LPS from a wide variety of solutions.

EXAMPLE 5

SEQUESTERING OF LPS FROM DIFFERING BACTERIAL SOURCES

Columns containing 100 ul (packed volume) of the matrix material of Example 1 were tested for the ability to sequester lipopolysaccharides from several bacterial strains. In each case, the purified LPS was labeled with $^{51}Cr$ and chromatographed on Sephadex to remove non-specifically bound $^{51}Cr$. 50 micrograms of LPS was applied to each column, then, the column washed with 20 bed volumes of water. The effluent was counted. The difference between radioactivity in the applied labeled-LPS solution and that in the washes indicates the efficiency of LPS removal.

| Source Bacteria for Lipopolysaccharide Preparation | % Removed |
|---|---|
| *Escherichia coli* | 97.3 |
| *Salmonella newington* | 96.3 |
| *Salmonella enteritidis* | 97.6 |
| *Yersinia enterocolitica* | 97.8 |
| *Salmonella Minnesota* | 94.6 |

This data demonstrates the efficacy of the invention in sequestering LPS from differing bacterial sources.

EXAMPLE 6

CONCENTRATION OF LPS FROM BIOLOGICAL FLUIDS AND RECOVERY

Normal plasma was contaminated with 20 ugm $^{51}Cr$ *E. coli* LPS per ml. The contaminated plasma was incubated at 37° C. for 3 hours to permit thorough association of endotoxin with the proteins.

100 ul of contaminated plasma, containing 2 ugm LPS, was applied to a 200 ul packed volume bed of SAB prepared as in Example 1. The column was washed with 0.15M saline solution, then the LPS eluted using 2 column volumes of a 2% solution of sodium desoxycholate (DOC) as elutant. The DOC was extracted by adding 6 volumes absolute ethanol, which precipitates the LPS. 5 ul of a 6% Dextran solution was added as a carrier for the LPS. The suspension was incubated on an ice bath for 20 minutes, then centrifuged in a clinical centrifuge for 5 minutes. The supernate was decanted and the pellet reconstituted in water. A portion of the water solution was counted to determine recovery as estimated by $^{51}Cr$. The other portion was assayed for LPS content using the Limulus Amoebocyte Lysate (LAL) test (Associates of Cape Cod).

Results
$^{51}Cr$ recovery - 50%
LAL

| Std. *E. coli* LPS | 500 pg | 50 pg | 25 pg | 12.5 pg |
|---|---|---|---|---|
| Test Response | 4+ | 4+ | 3+ | 2+ |

Thus, 50 pgm is the sensitivity of the test, that is, the point at which a firm clot is formed.

| Reconstituted Sample 1 ml Dilution | 1:10,000 | 1:20,000 | 1:40,000 |
|---|---|---|---|
| Test Response | 4+ | 4+ | 2+ |

Thus, a 1:20,000 dilution of the reconstituted sample contains 50 pg of LPS. Therefore, 50 pgm × 20,000 = 1 ugm. Since 2 ugm of the sample were applied to the column, the recovery of 1 ugm represents 50% of starting sample, in agreement with $^{51}Cr$ data.

This data establishes the utility of the invention in concentrating LPS from biological fluids and discloses a method of eluting it for quantitation.

EXAMPLE 7

OTHER DERIVATIVES WITH ENDOTOXIN ADSORBING UTILITY

Agarose-(isourea)-6-aminohexanoyl-p-benzamidinamide and Agarose-(isourea)-6-aminohexanoylanilide were prepared by the method of Example 1. These materials were loaded into columns and tested for their ability to sequester endotoxin as in the method of Example 1.

| Adsorbant Tested | % Adsorbed |
|---|---|
| Agarose (isourea)-6 aminohexanoyl-p-aminobenzamidinamide | 83.5 |
| Agarose (isourea)-6 aminohexanoyl-anilide | 94.3 |

Thus, aromatic substitutions for m-aminobenzamidine are also effective compositions for the removal of endotoxins.

EXAMPLE 8

PREPARATION AND TESTING OF AGAROSE-BASED, ETHER LINKED ADSORBANT

To facilitate the preparation of additional derivatives, 6-aminohexanoyl-meta-amidinoanilide (AB) was prepared. 61.9 mmoles of meta-amidinoaniline.HCl was dissolved in 100 ml water. The pH of the solution was adjusted to 3.8 by the addition of 1N NaOH. 133.8 mmoles of the carbobenzoxy-6-aminohexanoic acid was suspended in the solution. The suspension was cooled by placing it in an ice bath. 116 mmoles of 1-ethyl-3-(3-dimethylaminopropyl) carbodiimide was added as solids and the suspension stirred rapidly. The pH of the reaction mixture was maintained at 3.6 to 4.0 for four hours. The mixture was then allowed to warm to room temperature and stirred slowly overnight. The solids, crude carbobenzoxy-6-aminohexanoyl-m-amidinoanilide (C-AB), were filtered off, washed with water and dried. The crude product melted at 136° to 148° C. The C-AB was dissolved in glacial acetic acid and recrystallization caused by the addition of 10 volumes of absolute ethanol. The crystals were washed with ethanol and dried. 20.8 grams of C-AB melted at 206.5° to 208° C. (uncorrected) as expected, and co-chromatographed with an authentic sample.

The carbobenzoxy protecting group was removed by hydrogenation in the presence of palladium. After evaporation of the hydrogenation solvent, the solids were triturated with ether, yielding 7 grams of AB. The product melted at 181° to 183° C., uncorrected, as expected, and co-chromatographed with an authentic sample.

5 grams of epoxy-activated Sepharose 6B ™ was hydrated in water overnight. The solids were filtered and washed in the filter by percolation of water through the bed. The solids were transferred to a beaker with the addition of minimal water. The pH of the suspension was adjusted to 11.5 by the addition of $Na_2CO_3$ and NaOH. 1 gram of AB, above, was added to the suspension. The mixture was stirred overnight, then heated to 80° C. After cooling, the derivative was filtered and washed with water and 50% ethanol.

The derivatives in Example 8, 9 and 10 were tested using a tritium-labelled E. coli lipopolysaccharide (LPS) preparation, using 2 micrograms LPS per test.

| Adsorbant | Percent of LPS Bound |
| --- | --- |
| Epoxy-Sepharose 6B | 3.1 |
| AB Derivative of Expoxy-Sepharose 6B | 63.5 |
| Sepharose 4B | 13.8 |
| SAB | 85.6 |

The results with Sepharose 4B and SAB demonstrate the similarity of results obtained using tritium-labelled endotoxin and those obtained using $^{51}$Cr-labelled LPS. In addition, the utility of the ether-linked ligand is also shown.

EXAMPLE 9

PREPARATION OF GLASS-SUPPORTED BINDING AGENT 10 grams of succinylated controlled-pore glass, containing 1 millimole of carboxyl, was suspended in 25 ml dimethylformamide (DMF). 1 gram, 5 millimoles, of dicyclohexyl carbodiimide was added and the mixture stirred 30 minutes to permit formation of the active complex. 0.5 grams, 3.6 millimoles, of meta-nitrophenol was then added and the mixture stirred at 0° C. overnight to permit the formation of the nitrophenyl ester. The solids were filtered, washed with DMF, and a DMF solution containing 0.5 gm (3.6 millimoles) of meta-amidinoaniline added. The suspension was mixed for thirty minutes on ice, then stored at 4° C. to permit the formation of the Glass-Succinyl-Amidino-anilide (GSA). The derivative was filtered, washed with DMF, ethanol and water.

| Adsorbant | Percent of LPS Bound |
| --- | --- |
| Glass Succinate | 3.2 |
| Glass Succinate-AB Derivative | 8.8 |

The utility of glass to act as a support for the ligand is thus demonstrated.

EXAMPLE 10

PREPARATION OF POLY(STYRENE-2% BENZYL) ACYL AB 10 grams of poly (Styrene-2% benzyl chloride) was suspended in 20 ml absolute alcohol. 3 grams of AB, from above, was added as a solid. About 20 mg of phenolphthalein was added as a pH indicator. Saturated ethanolic NaOH was added dropwise until the first appearance of pink color. The solution was heated to boiling on a hotplate. The color disappeared, demonstrating the release of acid in the reaction. The pH was again titrated with NaOH until the pink color persisted. The solution was again heated to boiling. The pink color remained, demonstrating that the reaction of the benzyl chloride with the AB amine function had finished. The derivative was filtered and washed with ethanol and 50% ethanol.

| Adsorbant | Percent of LPS Bound |
| --- | --- |
| poly(Styrene-2% Benzyl-Cl) | 9.8 |
| poly(Styrene-2% Benzyl-AB) | 19.0 |

Thus, the utility of poly styrene as the support for the ligand is established and the utility of secondary amine coupling of the ligand to the support is shown.

EXAMPLE 11

PREPARATION OF AGAROSE-SUPPORTED BINDING AGENTS WITH VARYING SPACER LENGTHS

Agarose was derivatized by the method of Example 1, using spacers containing methylene groups varying in number from 1 to 11. Each derivative was tested for its ability to bind $^{51}$Cr-labelled E. coli lipopolysaccharide by the method of Example 1. The parent agarose, ethanolamine agarose and 6-aminohexanoic acid agarose, representative of incompletely reacted intermediates possibly present, were also tested to provide a base for comprison with the completed derivatives.

| Derivative Number in this test | Description of the Derivative | % Bound |
| --- | --- | --- |
| I | Agarose | 4.0 |
| II | Agarose-(isourea)-2-aminoethanol | 3.0 |
| III | Agarose-(isourea)-6-aminohexanoic acid | 4.0 |

-continued

| Derivative Number in this test | Description of the Derivative | % Bound |
|---|---|---|
| IV | Agarose-(isourea)-2-aminoacetyl-m-amidinoanilide | 17.0 |
| V | Agarose-(isourea)-4-aminobutyryl-m-amidinoanilide | 94.0 |
| VI | Agarose-(isourea)-5-aminovaleryl-m-amidinoanilide | 75.0 |
| VII | Agarose-(isourea)-6-aminocaproyl-m-amidinoanilide | 90.0 |
| VIII | Agarose-(isourea)-7-aminocapryllyl-m-amidinoanilide | 59.0 |
| IX | Agarose-(isourea)-12-aminododecanoyl-m-amidinoanilide | 94.0 |

The endotoxin binding utility of the compounds representing the invention with 1 to 11 methylene groups in the spacer is thus demonstrated.

Similarly, it is shown that incompletely formed derivatives do not have significant ability to bind endotoxin.

A measurement of the capacity of these derivative to adsorb endotoxin was performed. This test was achieved by repeatedly challenging small columns of each derivative with $^{51}$Cr-labelled endotoxin, washing the column and counting to determine the breakthrough and amount retained. When the breakthrough was equivalent to the challenge applied, the column was considered to be saturated to its capacity. This test was performed on each derivative with endotoxins prepared from 16 different gram-negative bacteria.

The amount of endotoxin bound (micrograms) was divided by the volume of the derivative (microliters) and the resulting value, micrograms endotoxin adsorbed per microliter derivative, represented the capacity of the derivative.

| Bacterial Lipopolysaccharide Source | ugm endotoxin bound per ul of derivative number; | | | | | | | | |
|---|---|---|---|---|---|---|---|---|---|
| | I | II | III | IV | V | VI | VII | VIII | IX |
| B. fragilis | 0.07 | 0.07 | 0.07 | 0.09 | 0.57 | 0.47 | 0.47 | 0.43 | 0.57 |
| E. coli 0113 | 0.006 | 0.009 | 0.007 | 0.03 | 0.54 | 0.40 | 0.51 | 0.38 | 0.52 |
| Ps. aeruginosa | 0.12 | 0.11 | 0.12 | 0.12 | 0.51 | 0.47 | 0.60 | 0.52 | 0.68 |
| N. lactamica | 0.19 | 0.15 | 0.16 | 0.21 | 0.89 | 0.79 | 0.47 | 0.46 | 0.83 |
| S. enteritidis | 0.09 | 0.08 | 0.08 | 0.16 | 0.69 | 0.71 | 0.91 | 0.79 | 0.64 |
| S. marcescens | 0.07 | 0.06 | 0.06 | 0.08 | 0.45 | 0.35 | 0.37 | 0.33 | 0.54 |
| Ps. flourescens | 0.13 | 0.08 | 0.09 | 0.14 | 0.46 | 0.46 | 0.24 | 0.26 | 0.57 |
| Sh. dysenteriae | 0.06 | 0.06 | 0.06 | 0.08 | 0.58 | 0.44 | 0.46 | 0.46 | 0.53 |
| Pr. morganii | 0.10 | 0.09 | 0.10 | 0.13 | 0.60 | 0.53 | 0.58 | 0.53 | 0.67 |
| Pr. vulgaris | 0.07 | 0.06 | 0.06 | 0.08 | 0.50 | 0.42 | 0.54 | 0.41 | 0.46 |
| Kl. oxytoca | 0.04 | 0.02 | 0.03 | 0.10 | 0.63 | 0.58 | 0.61 | 0.59 | 0.75 |
| Prov. stuartii | 0.10 | 0.03 | 0.07 | 0.15 | 0.61 | 0.74 | 0.76 | 0.62 | 0.80 |
| Ent. cloacae | 0.008 | 0.01 | 0.01 | 0.06 | 0.38 | 0.32 | 0.38 | 0.32 | 0.36 |
| kl. pneumoniae | 0.01 | 0.02 | 0.02 | 0.06 | 0.38 | 0.29 | 0.35 | 0.29 | 0.42 |
| Pr. mirabilis | 0.08 | 0.07 | 0.06 | 0.11 | 0.54 | 0.44 | 0.49 | 0.48 | 0.53 |
| Yer. enterocolitica | 0.04 | 0.04 | 0.05 | 0.11 | 0.75 | 0.67 | 0.81 | 0.67 | 0.72 |

It is thus shown that the intermediates in the preparation of the invention have but small capacity for binding lipopolysaccharides. The compounds representing the invention have much greater capacities and bind lipopolysaccharides from a broad spectrum of bacteria.

What is claimed is:

1. A matrix material for binding endotoxins, said matrix material having the formula:

A-x-B-y-Z wherein

A is a water insoluble, high molecular weight polymer;

x is an O, N, disubstituted isourea, an oxycarbonyl, oxo, aminocarbonyl or amino group;

B is alkyl of from 3 to 12 carbon atoms;

y is an oxo, aminocarbonyl or amino group; and

Z is selected from the group consisting of phenyl, naphthyl, benzyl, or a group consisting of substituted phenyl, substituted naphthyl and substituted benzyl, said substituted groups being substituted with amidino, guandino, amino, carboxamido, halo, nitro, alkyl, or alkoxy groups.

2. The matrix material of claim 1 wherein said polymer is selected from the group consisting of cellulose, cellulose acetate, cellulose nitrate, agarose, polymethacrylate, polystyrene and glass.

3. The matrix material of claim 1 wherein A is agarose, x is an O, N, disubstituted isourea, B is alkyl of 5 carbon atoms, y is aminocarbonyl and Z is phenyl m-amidine.

4. The matrix material of claim 1 wherein A is a water insoluble polymer selected from the group consisting of cellulose, cellulose acetate, cellulose nitrate agarose, polymethacrylate, polystyrene and glass, x is an O, N, disubstituted isourea, B is alkyl of 3 to 12 carbon atoms, y is methylene, oxo, amino or aminocarbonyl, and Z is phenyl, naphthyl or benzyl substituted by tertiary ammonium, amidinium, or halo.

5. The matrix material of claim 1 wherein A is cellulose, x is amino, B is alkyl of 3 to 12 carbon atoms, y is amino or aminocarbonyl, and Z is phenyl or benzyl substituted by amidino.

* * * * *